(12) United States Patent
Wang et al.

(10) Patent No.: US 10,499,870 B2
(45) Date of Patent: Dec. 10, 2019

(54) METHODS AND APPARATUSES FOR QUANTIFYING VASCULAR FLUID MOTIONS FROM DSA

(71) Applicant: The Chinese University of Hong Kong, Hong Kong (CN)

(72) Inventors: Defeng Wang, Hong Kong (CN); Ka Long Ko, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 208 days.

(21) Appl. No.: 15/600,493

(22) Filed: May 19, 2017

(65) Prior Publication Data

US 2018/0333123 A1    Nov. 22, 2018

Related U.S. Application Data

(63) Continuation-in-part of application No. 15/600,387, filed on May 19, 2017, now abandoned.

(51) Int. Cl.
*A61B 6/00* (2006.01)
*G06T 7/00* (2017.01)
(Continued)

(52) U.S. Cl.
CPC ............ *A61B 6/5217* (2013.01); *A61B 6/481* (2013.01); *A61B 6/482* (2013.01); *A61B 6/487* (2013.01); *A61B 6/504* (2013.01); *A61B 6/507* (2013.01); *A61B 6/5235* (2013.01); *G06T 7/0012* (2013.01); *G06T 7/254* (2017.01); *G06T 7/269* (2017.01); *G06T 2207/10016* (2013.01); *G06T 2207/10064* (2013.01); *G06T 2207/20016* (2013.01); *G06T 2207/20224* (2013.01); *G06T 2207/30101* (2013.01);
(Continued)

(58) Field of Classification Search
CPC ....... A61B 6/5217; A61B 6/481; A61B 6/487; A61B 6/507; A61B 6/482; A61B 6/5235; A61B 6/504; G06T 7/0012; G06T 7/254; G06T 2211/424; G06T 2211/404; G06T 2207/30101
See application file for complete search history.

(56) References Cited

U.S. PATENT DOCUMENTS

| 2009/0028403 A1* | 1/2009 | Bar-Aviv | G06F 19/321 |
| | | | 382/128 |
| 2011/0033102 A1* | 2/2011 | Zhu | G06T 7/0016 |
| | | | 382/134 |
| 2015/0358637 A1* | 12/2015 | Jacquelin | H04N 19/513 |
| | | | 382/107 |

* cited by examiner

*Primary Examiner* — Vincent Rudolph
*Assistant Examiner* — Pinalben Patel
(74) *Attorney, Agent, or Firm* — Leydig, Voit & Mayer, Ltd.

(57) ABSTRACT

Disclosed is a method and an apparatus for quantifying vascular fluid motions from digital subtraction angiography (DSA) images, comprising: calculating an optical flow field between two temporal consecutive DSA images; and estimating a displacement of blood or tissue between the two temporal consecutive DSA images from the calculated optical flow field, wherein the optical flow field is calculated by solving a minimization problem of a CLG energy function, wherein the CLG energy function combines the temporally extended variant of Horn-Schunck approach with Lucas-Kanade approach non-linearly in spatiotemporal approach. The present disclosure provides a new optical flow solution significantly reducing the computation cost with a high robustness for quantifying vascular fluid motions from DSA.

18 Claims, 6 Drawing Sheets

(51) Int. Cl.
*G06T 7/254* (2017.01)
*G06T 7/269* (2017.01)
(52) U.S. Cl.
CPC ............... *G06T 2207/30104* (2013.01); *G06T 2211/404* (2013.01); *G06T 2211/424* (2013.01)

METHODS AND APPARATUSES FOR QUANTIFYING VASCULAR FLUID MOTIONS FROM DSA

CROSS-REFERENCE TO RELATED APPLICATION

This patent application is a continuation-in-part of co-pending U.S. patent application Ser. No. 15/600,387 filed May 19, 2017, and entitled "METHODS AND APPARATUSES FOR QUANTIFYING VASCULAR FLUID MOTIONS FROM DSA", which is incorporated in its entirety by this reference.

TECHNICAL FIELD

The disclosure relates to hemodynamic and computer vision technology, in particular, to methods and apparatuses for quantifying vascular fluid motions from DSA.

BACKGROUND

Hemodynamic feature is an important clinical diagnostic parameter which provides critical information for cerebrovascular diseases. Currently, several approaches are applied to measure arteriovenous flow, including computed tomographic (CT) perfusion, magnetic resonance (MR) perfusion, phase-contrast magnetic resonance image (PC-MRI) and Doppler ultrasound. However, each of the above-mentioned technique does not fully satisfying the clinical requirements. For example, patient undergo CT imaging would need to expose to a high dose of radiation, with MR imaging would require a long image acquisition duration. Though Doppler ultrasound is a clinical routine vessel flow quantification method, the modality is limited due to its poor spatial resolution with significant attenuation after passing through skull. PC-MRI technique is a newly released flow quantification technique as a form of magnetic resonance angiography (MRA). The method allows an indirect measurement of in vivo blood flows with non-invasive and non-radiation exposure. However, the spatial-temporal resolution of PC-MRI is still limited, which could not effectively measure fast-changing and complicated flow situations.

Digital subtraction angiography (DSA) is a fluoroscopy technique that commonly used in interventional radiology. The term "subtraction" is referred as subtracting images with contrast medium by "pre-contrast images". The technique is suitable for detecting cardiovascular and cerebrovascular arterial obstruction by visualizing blood flow with introducing of radiopaque iodine intravenously. Conventionally DSA is a clinical gold standard for arterial imaging for its high spatial and temporal resolution. The imaging method assesses hemodynamic vascular structures with only gray scales, including the detection of arterial occlusions, arterial stenosis, cerebral aneurysm and arteriovenous malformations. Several vendors have provided velocity color coding visualization software (Siemens Syngo iFlow, General Electric AngioViz, Philips 2D Perfusion).

Optical flow is a widely used computer vision algorithm that detects the pattern of apparent motion of objects, surfaces, and edges in a visual scene. The algorithm was firstly introduced by American psychologist James J. Gibson in the 1940s. The original concept was to study visual stimulus for movement perception, shape and distance perception, and control of locomotion. It is currently used by image processing for motion detection and object segmentation. Shpilfoygel et al. reviewed more than 100 manuscripts and illustrated the advantage of combining optical flow and DSA. Up to 2014, two major methods were applied in flow quantification, namely image density analysis and Lucas-Kanade optical flow method.

Another widely adopted Horn-Schunck optical flow method solve the velocity field with the minimization of global optical flow energy function. The method could linearly combine with Lucas-Kanade approach to include both local and global information. However, both Horn-Schunck and Lucas-Kanade method are developed on the basis of Brightness Constancy assumption. A large displacement of objects could cause the calculation error. A multi-resolution strategy could be a solution to the problem.

SUMMARY

The present disclosure aims to provide a new optical flow solution significantly reducing the computation cost with a high robustness for quantifying vascular fluid motions from DSA.

According to an aspect of the present disclosure, a method for quantifying vascular fluid motions from DSA, comprising: calculating an optical flow field between two temporal consecutive DSA images; and estimating a displacement of blood or tissue between the two temporal consecutive DSA images from the calculated optical flow field, wherein the optical flow field is calculated by combining a temporally extended variant of Horn-Schunck approach with Lucas-Kanade approach non-linearly in spatiotemporal approach under a multiresolutional scheme. Wherein calculating an optical flow field between two temporal consecutive DSA images comprising: setting a plurality of image pyramid levels from coarse to fine; at each of the plurality of image pyramid levels, calculating an optical flow increment between the two temporal consecutive DSA images which minimizes a CLG energy function, wherein the CLG energy function combines the temporally extended variant of Horn-Schunck approach with Lucas-Kanade approach non-linearly in spatiotemporal approach; and calculating an interpolated sum of the optical flow increments calculated over all the plurality of image pyramid levels so as to obtain the optical flow field. The CLG energy function is established by extending the classically Horn-Schunck approach. A Gaussian smoothing term is introduced to the energy function where the original energy term is an estimation to the optical flow increment and is determined by the gradient of image intensity field. The intensity field is extended from spatial field to the spatial-temporal field according to the two temporal consecutive DSA images. In Lucas-Kanade approach the localized flow is assumed to be constant and represented as a Gaussian kernel convolution in the CLG energy function.

According to another aspect of the present disclosure, an apparatus for quantifying vascular fluid motions from DSA, a first unit configured to calculate an optical flow field between two temporal consecutive DSA images; and a second unit configured to estimate a displacement of blood or tissue between the two temporal consecutive DSA images from the calculated optical flow field, wherein the optical flow field is calculated by solving a minimization problem of a CLG energy function, wherein the CLG energy function combines the temporally extended variant of Horn-Schunck approach with Lucas-Kanade approach non-linearly in spatiotemporal approach. The first unit comprises a level setting sub-unit configured to set a plurality of image pyramid levels from coarse to fine; a first calculating sub-unit configured to calculate an optical flow increment between the two temporal consecutive DSA images which minimizes the CLG energy function at each of the plurality of image pyramid levels; and a second calculating sub-unit configured to calculate an interpolated sum of the optical flow increment fields calculated over all the plurality of image pyramid levels so as to obtain the optical flow field. The CLG energy function is established by extending the classically Horn-Schunck approach. A Gaussian smoothing term is introduced to the energy function where the original energy term is an estimation to the optical flow increment and is determined by the gradient of image intensity field. The intensity field is extended from spatial field to the spatial-temporal field according to the two temporal consecutive DSA images. In Lucas-Kanade approach the localized flow is assumed to be constant and represented as a Gaussian kernel convolution in the CLG energy function. The first calculating sub-unit comprises a successive over-relaxation sub-unit configured to solve the minimization problem of the CLG energy function by successive over-relaxation approach. The successive over-relaxation sub-unit comprises an initialization sub-unit configured to setting an initial optical flow field, an iteration sub-unit configured to iteratively renew the optical flow field, and a stopping sub-unit configured to stop the iteration and obtain a final optical flow field at current pyramid level when the criterion for stopping iteration is met.

DETAILED DESCRIPTION OF EMBODIMENTS

Hereinafter, embodiments of the present disclosure will be described with reference to the accompanying drawings.

The present application will be further described below in detail in combination with the accompanying drawings and the embodiments. It should be appreciated that the specific embodiments described herein are merely used for explaining the relevant invention, rather than limiting the invention. In addition, it should be noted that, for the ease of description, only the parts related to the relevant invention are shown in the accompanying drawings.

It should also be noted that the embodiments in the present application and the features in the embodiments may be combined with each other on a non-conflict basis. The present application will be described below in detail with reference to the accompanying drawings and in combination with the embodiments.

According to an embodiment of the present disclosure, a method for quantifying vascular fluid motions from DSA is provided. The method comprises: calculating an optical flow field between two temporal consecutive DSA images; and estimating a displacement of blood or tissue between the two temporal consecutive DSA images from the calculated optical flow field. Wherein the optical flow field is calculated by solving a minimization problem of a CLG energy function, wherein the CLG energy function combines the temporally extended variant of Horn-Schunck approach with Lucas-Kanade approach non-linearly in spatiotemporal approach.

According to another embodiment of the present disclosure, calculating the optical flow field comprising: setting a plurality of image pyramid levels from coarse to fine; at each of the plurality of image pyramid levels, calculating an optical flow increment between the two temporal consecutive DSA images which minimizes the CLG energy function; and calculating an interpolated sum of the optical flow increment fields calculated over all the plurality of image pyramid levels so as to obtain the optical flow field.

Figure 1:
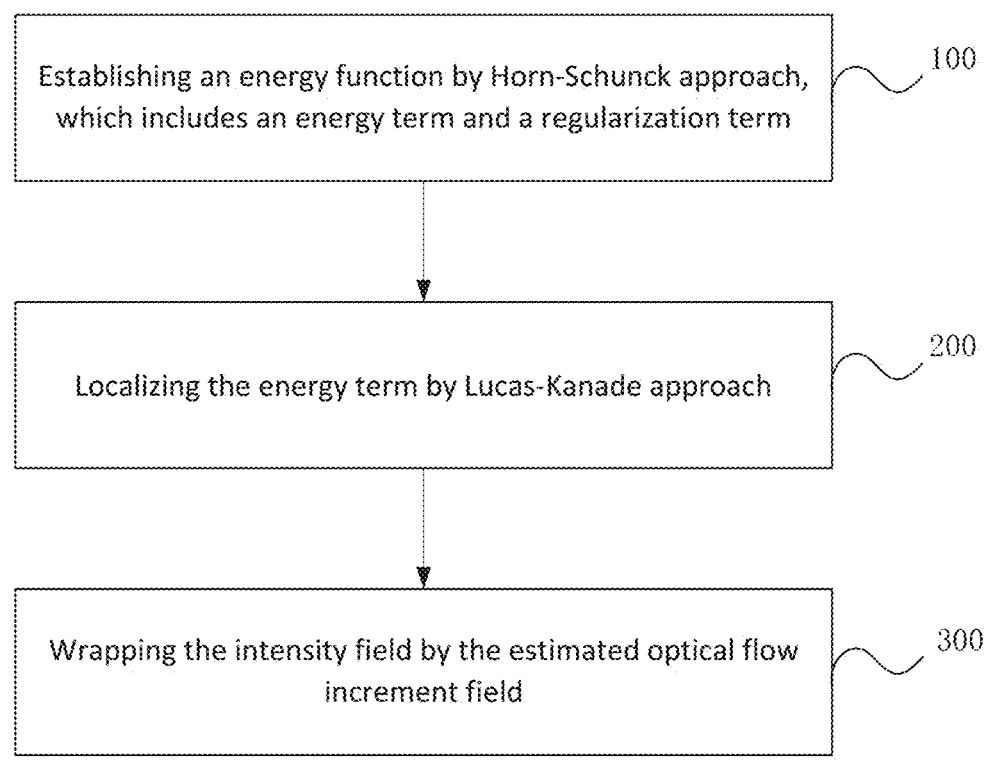
FIG. 1 illustrates a flowchart of the method for establishing a CLG energy function according to an embodiment of the present disclosure.

Furthermore, FIG. 1 illustrates a procedure for establishing the CLG energy function according to an embodiment of the present disclosure, the CLG energy function is established as follow:

Step 100: establishing an energy function by Horn-Schunck approach, which includes an energy term and a regularization term; wherein the energy term is determined by an estimated optical flow increment field and a gradient of an intensity field, the intensity field is extended from a spatial field to a spatial-temporal field according to the two temporal consecutive DSA images.

Horn-Schunck method assumes a smooth optical flow over the whole image throughout time. The method aims to minimize the distortions in the optical flow. By integrating, an energy function of the flow is formulated as global energy function and try to minimize the function with regularization parameter a.

The fundamental theory of optical flow field algorithm is Brightness Constancy. For a 2D-Ft pixel at local p=[x, y, t]$^T$ with intensity I(p)=I(x,y,t), after a spatial time variation $\Delta x$, $\Delta y$ and $\Delta t$, the brightness does not change, it is written as follow:

$$I(x,y,t)=I(x+\Delta x, y+\Delta y, t+\Delta t) \quad (1)$$

The equation is solved by Vedula et al. with first-order Taylor series expansion:

$$I(x+\Delta x, y+\Delta y, t+\Delta t) = I(x,y,t) + \frac{\partial I}{\partial x}\Delta x + \frac{\partial I}{\partial y}\Delta y + \frac{\partial I}{\partial t}\Delta t \quad (2)$$

It is obvious that $$\frac{\partial I}{\partial x}\|u\| + \frac{\partial I}{\partial y}\|v\| + \frac{\partial I}{\partial t} = 0 \quad (3)$$

u and v are the x and y velocity component respectively. For simplicity, $I_i$ would denote for the spatial or temporal derivatives of image intensity I, $$\text{i.e. } I_x = \frac{\partial I}{\partial x}, I_y = \frac{\partial I}{\partial x} \text{ and } I_t = \frac{\partial I}{\partial t}.$$

The Brightness Constancy could be achieved by setting $I_t=0$. However, in the present embodiment, the intensity field is extended from a spatial field to a spatial-temporal field according to the two temporal consecutive DSA images, hence $I_t$ need to be considered, then the energy function is written as follow:

$$E_{HS} = \iint [(I_x\|u\| + I_y\|v\| + I_t)^2 + \alpha(\|\nabla u\|^2 + \|\nabla v\|^2)]dxdy \quad (2)$$

Wherein the part of $(I_x\|u\| + I_y\|v\| + I_t)^2$ is called the energy term for convenience, and the part of $\alpha(\|\nabla u\|^2 + \|\nabla v\|^2)$ is called the regularization term.

A larger $\alpha$ leads to smoother flow, which is associated with the magnitude of gradient over the velocity field. The term $\alpha$ is represented as $\alpha^2$ in the original article, where modified to $\alpha$ in the combined local-global optical flow manuscript.

Step 200: localizing the energy term in current energy function by Lucas-Kanade approach.

Lucas-Kanade method assumed a localized constant flow within a size of $\rho$. It is expressed by a convolution kernel. According to Lucas-Kanade method, the energy term is transformed to a convolution with an Gaussian kernel $K_\rho$ with standard deviation $\rho$ by a least squares criterion. It is written as follow:

$$E_{LK} = K_\rho * (I_x\|u\| + I_y\|v\| + I_t) \quad (3)$$

With $\nabla_3 I := [I_x, I_y, I_t]^T$ and optical flow field as $w=[u(p), v(p), 1]^T$, the HS energy function is rewritten as $$E_{HS}(w) = \iint [w^T(\nabla_3 I \nabla_3 I^T)w + \alpha(\|\nabla u\|^2 + \|\nabla v\|^2)]dxdy \quad (4)$$

Furthermore, a localized spatial-temporal derivative smoothing term $J_\rho(\nabla_3 I) = K_\rho * (\nabla_3 I \nabla_3 I^T)$ is introduced in the Combined Local-Global (CLG) optical flow approach, and express the energy function as $$E_{CLG}(w) = \iint [w^T J_\rho(\nabla_3 I)w + \alpha(\|\nabla u\|^2 + \|\nabla v\|^2)]dxdy \quad (5)$$

wherein $\rho$ denotes for a localized constant flow assumed in Lucas-Kanade approach, $K_\rho$ denotes for a Gaussian kernel with standard deviation $\rho$, I denotes for the intensity field of DSA images, $\nabla_3 I = [I_x, I_y, I_t]^T$, denoting for the gradient of the intensity field of DSA images, wherein $$I_x = \frac{\partial I}{\partial x}, I_y = \frac{\partial I}{\partial y} \text{ and } I_t = \frac{\partial I}{\partial t},$$

x and y denote for a two-dimensional spatial position, t denotes for a time.

When $\rho=0$ the CLG energy function with no localized smoothing occurs, the CLG function returns to the HS energy function. Meanwhile, when $\alpha=0$, the function would be equivalent to LK method.

The CLG energy function so far includes the local and global information with a spatial smoothing term $J_\rho$. However, in order to fulfill Brightness Constancy assumption, the vector field w need to be small. For images with large object displace would appear to be discontinuities and caused error, multiresolutional strategies are introduced to solve this problem. The image is successively computed from coarse to fine level, yields a more accurate optical flow field.

Step 300: wrapping the intensity field in the energy term of current energy function by the estimated optical flow increment field.

The multiresolutional approach is computed with an image pyramid with decreasing size of images. The approach starts from the smallest (coarsest) image to the largest (finest) image. The optical flow field computed in coarser level is used to warp the moved image. In the two consecutive frames $I_1$ and $I_2$ situation at time point $t_1$ and $t_2$, the wrapped image of $I_2$ may denote as $I(x+\delta u, y+\delta v)=I(p+\delta w)$. At each level of image pyramid the optical flow increment field is computed ($\delta w$). The final optical flow field estimation is the interpolated sum of all optical flow increment field estimations over the pyramid levels. The energy function of the multiresolutional optical flow at image pyramid level m is written as:

$$E_{CLG-MS}(\delta w^{(m)}) = \iint [\delta w^{(m)T} J_\rho^{(m)}(\nabla_3 I(p+\delta w^{(m)}))\delta w^{(m)} + \alpha(\|\nabla(w^{(m)} + \delta w^{(m)})\|^2)]dxdy \quad (6)$$

In this energy function, the localized spatial-temporal derivative smoothing tensor is further defined as a term determined by $\nabla_3 I(p+\delta w^{(m)})$, wherein p denotes for a spatial-temporal position including the two-dimensional spatial position and the time point, $\delta w^{(m)}$ denotes for a estimated optical flow increment field at an image pyramid level m, $I(p+\delta w^{(m)})$ denotes for the second DSA image wrapped by $\delta w^{(m)}$. The regularization term is defined as $\alpha(\|\nabla(w^{(m)} + \delta w^{(m)})\|^2)$, wherein $\alpha$ denotes for the regularization parameter, $w^{(m)}$ denotes for a optical flow field at the image pyramid level m, $w^{(m)} + \delta w^{(m)}$ denotes for the optical flow field at the image pyramid level m wrapped by $\delta w^{(m)}$.

The multiresolutional scheme can be generally applied to any optical flow methods, with the parameters to adjust the number of scales and the scaling factor.

Furthermore, in another embodiment, the minimization problem of the CLG energy function is solved by successive over-relaxation approach. The successive over-relaxation approach comprising: at each image pyramid level, setting an initial optical flow field; iteratively renew the optical flow field, wherein in each iterative step, a new velocity at pixel i within the image domain is determined by a current velocity at the pixel i, relaxation parameter $\omega$, a current velocity at neighbor pixels of the pixel i, the localized spatial-temporal derivative smoothing tensor, and the regularization term $\alpha$; and stopping the iteration and obtaining a final optical flow field at current pyramid level when the criterion for stopping iteration is met.

A typical minimization of Horn-Schunck optical flow energy function is the Euler-Lagrange method. By denoting $J_{nm}$ as the (n,m) component of tensor $J_\rho(\nabla_3 I)$. The minimization of equation (9) would satisfy the following system of partial differential equations:

$$\Delta(\delta u)^{(m)} - \frac{1}{\alpha}(J_{11}^{(m)}\delta u^{(m)} + J_{12}^{(m)}\delta v^{(m)} + J_{13}^{(m)}) = 0 \quad (7)$$

$$\Delta(\delta v)^{(m)} - \frac{1}{\alpha}(J_{12}^{(m)}\delta u^{(m)} + J_{22}^{(m)}\delta v^{(m)} + J_{23}^{(m)}) = 0$$

Let N(i) denotes a set of 4 neighbor pixels $i \in [1, \ldots, N]$. The finite difference approximation of equation (10) is given by. This sparse linear system of equations could be solved iteratively by SOR method.

$$\sum_{j \in N(i)} \frac{\delta u_j^{(m)} - \delta u_i^{(m)}}{h^2} - \frac{1}{\alpha}(J_{11i}^{(m)}\delta u_i^{(m)} + J_{12i}^{(m)}\delta v_i^{(m)} + J_{13i}^{(m)}) \quad (11)$$

$$\sum_{j \in N(i)} \frac{\delta v_j^{(m)} - \delta v_i^{(m)}}{h^2} - \frac{1}{\alpha}(J_{21i}^{(m)}\delta u_i^{(m)} + J_{22i}^{(m)}\delta v_i^{(m)} + J_{23i}^{(m)})$$

This sparse linear system of equations could be solved iteratively by SOR method. The approach is simple with high efficiency. Now the upper case index would denote for the iteration step, multiresolutional SOR method iteration scheme is as following:

$$u_i^{(k+1,m)} = (1-\omega)u_i^{(k,m)} +$$

$$\omega \left[ \frac{\sum_{j \in N^-(i)} u_j^{(k+1,m)} + \sum_{j \in N^+(i)} u_j^{(k,m)} - \frac{h^2}{\alpha}\left(J_{12i}^{(m)} v_i^{(k,m)} + J_{13i}^{(m)}\right)}{|N(i)| + \frac{h^2}{\alpha} J_{11i}^{(m)}} \right]$$

$$v_i^{(k+1,m)} = (1-\omega)v_i^{(k,m)} +$$

$$\omega \left[ \frac{\sum_{j \in N^-(i)} v_j^{(k+1,m)} + \sum_{j \in N^+(i)} v_j^{(k,m)} - \frac{h^2}{\alpha}\left(J_{22i}^{(m)} u_i^{(k+1,m)} + J_{23i}^{(m)}\right)}{|N(i)| + \frac{h^2}{\alpha} J_{22i}^{(m)}} \right];$$

Where $$N^-(i) := \{j \in N(i) \mid j < i\} \quad (8)$$
$$N^+(i) := \{j \in N(i) \mid j > i\}$$

The term |N(i)| accounts for the numbers of neighbor pixels at the pixel i within the image domain. $\omega \in (0,2)$ is called relaxation parameter which influences convergence speed, here we set between 1.9 to 1.99. When $\omega=1$ the finite iteration becomes the well know Gauss-Seidei method. The initialization of flow field is not critical to computational result as the method is globally convergent. Hence it is safe to set initial flow field to 0.

Figure 2:
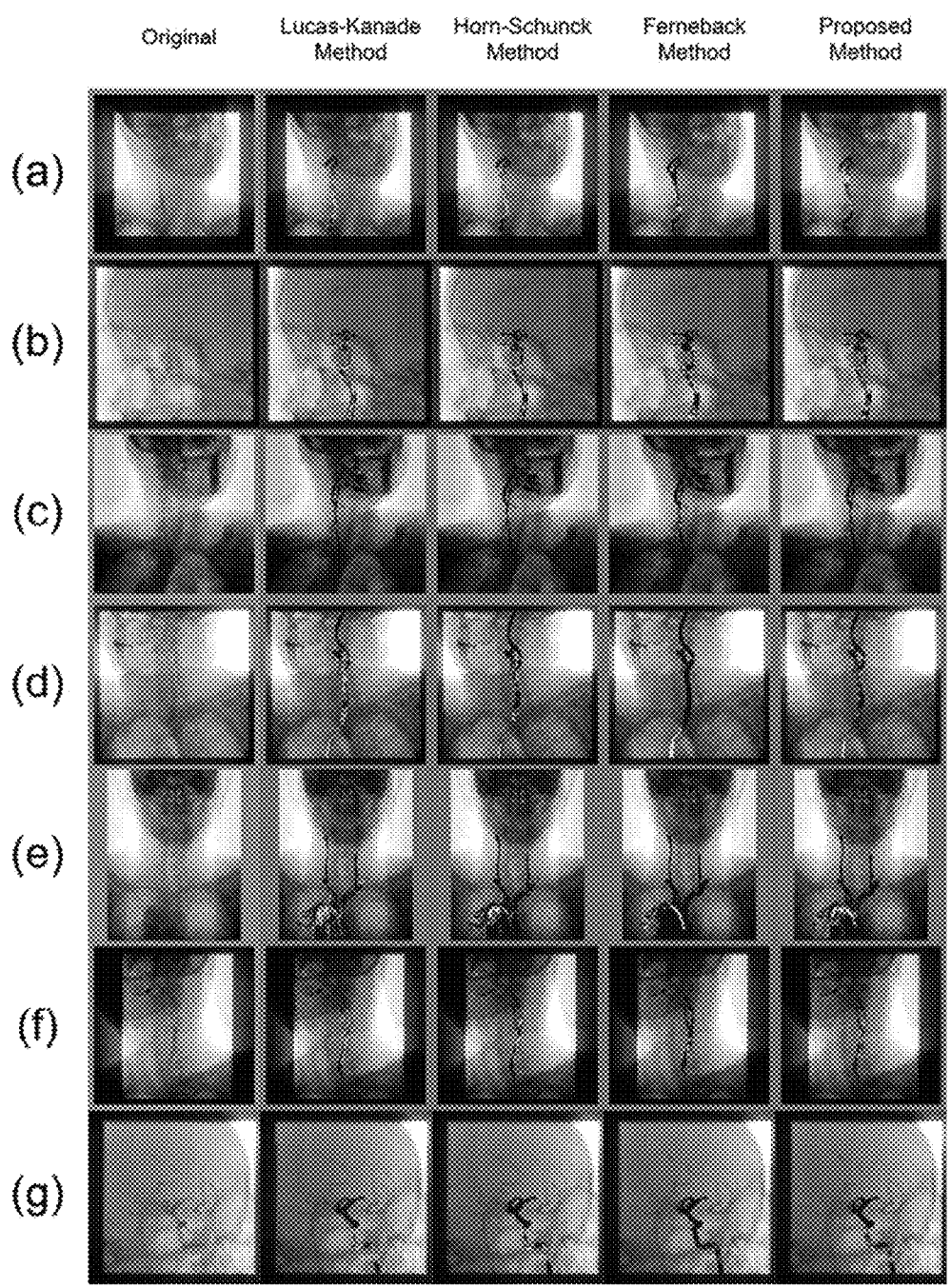
FIG. 2 illustrates a visualization of contrast flow velocity magnitude using different optical flow methods.

The contrast flow velocity magnitude by using different optical flow methods were shown in FIG. 2. Apart from the proposed optical flow scheme, conventional motion detections on same data are computed by OpenCV. The control methods include Lucas-Kanade, Horn-Schunck, and Gunnar Farneback's algorithm.

In Lucas-Kanade method, the size averaging window used for grouping pixels is set to be a square shape with 15 pixels one each dimension. The Horn-Schunck method would terminate the iterations whenever total iterations reach 500 or residual value is less than 0.0001. The regularization parameter, or called smoothness weight in OpenCV algorithm, was set at 0.012. In Farneback's method, the algorithm adopted a pyramids scheme with customized pyramid scale at 0.75 with 3 levels depth. Average window size was set the same as Lucas-Kanade method. For each pyramid level, the algorithm will iterate for 20 times with the first input as the initial flow approximation. A total of 5 neighbor pixels was used to find the polynomial expansion in each pixel, with a Gaussian smoothing standard deviation at 1.2.

In the proposed method, regularization parameter was set at 0.0006. The pyramid scale was set at 0.55 with a minimum window size of 256 pixels on each side, which was equivalent to a size of 3 level depth pyramid image in Farneback's method. SOR was iterated for 20 times on each pyramid level.

The algorithms were implemented over a quad core PC (3.40 GHz) without GPU acceleration. The average computation time for different methods with the 7 DSA series is tabulated in Table 1. Table 1 shows average computation time for one slice using different motion tracking methods. Unit is in second. In comparison with traditional Horn-Schunck method, a significant reduction in computation speed from ~5 seconds to ~2 seconds was measured. The speed of proposed method was comparable with Farneback's optical flow estimation, while the localized Lucas-Kanade method is more suitable for rapid applications.

TABLE 1

| Case | Lucas-Kanade | Horn-Schunck | Farneback | Proposed |
| --- | --- | --- | --- | --- |
| (a) - pre-stenting | 0.10 | 4.95 | 2.00 | 2.09 |
| (b) - post-stenting | 0.09 | 5.09 | 1.91 | 2.00 |
| (c) | 0.09 | 5.78 | 1.80 | 1.93 |
| (d) | 0.09 | 4.86 | 1.91 | 2.00 |
| (e) | 0.09 | 4.75 | 1.92 | 1.99 |
| (f) | 0.10 | 5.52 | 2.62 | 2.14 |
| (g) | 0.09 | 5.22 | 1.98 | 2.06 |
| (h) | 0.09 | 4.81 | 1.85 | 1.98 |
| Grand average | 0.09 | 5.12 | 2.00 | 2.02 |

Figure 3:
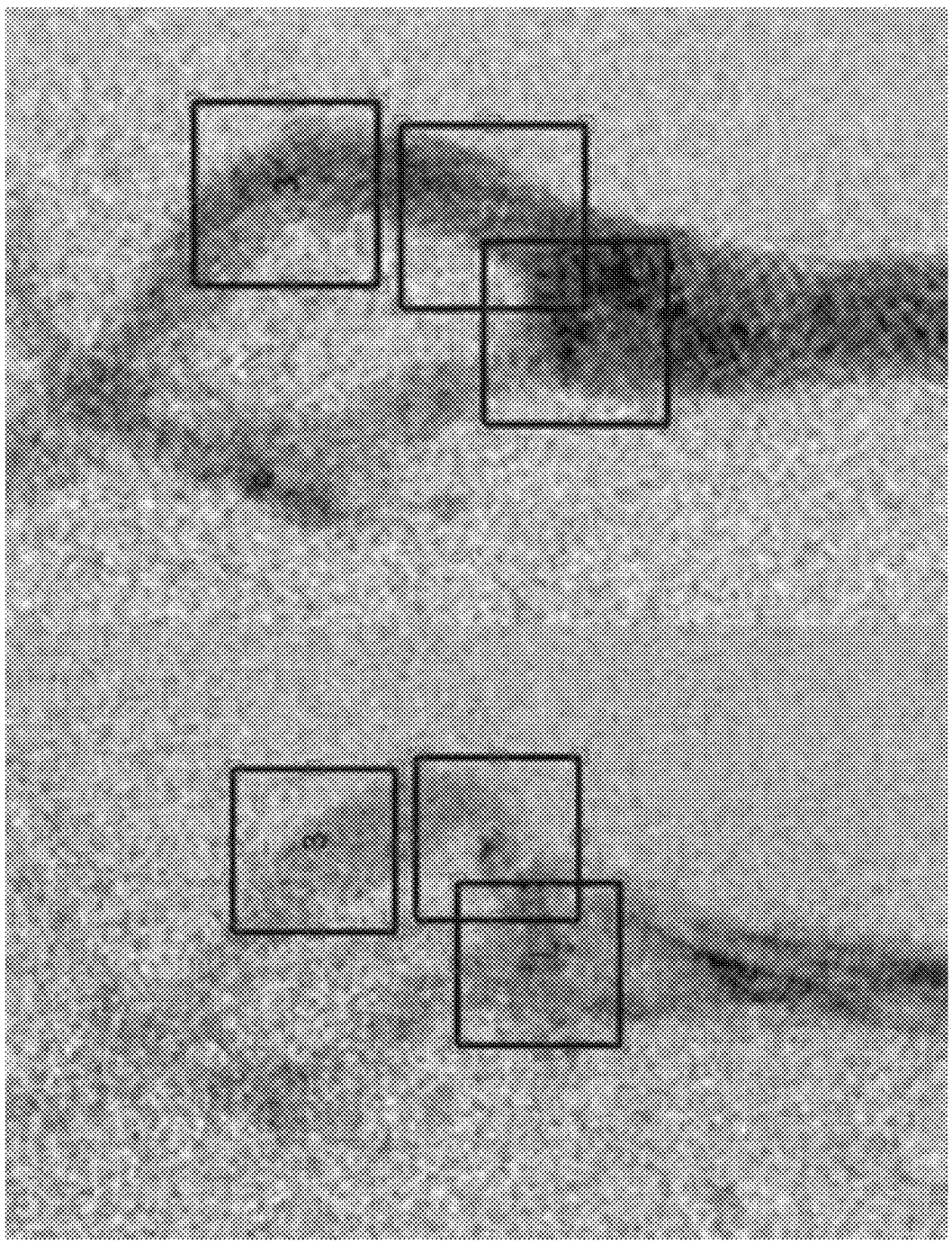
FIG. 3 illustrates an example showcase of localized velocity flows profiling before and after stenting; wherein ROI 1 represents a region before stenosis, ROI 2 represents a stenosis, ROI 3 represents a region after stenosis.
Figure 4:
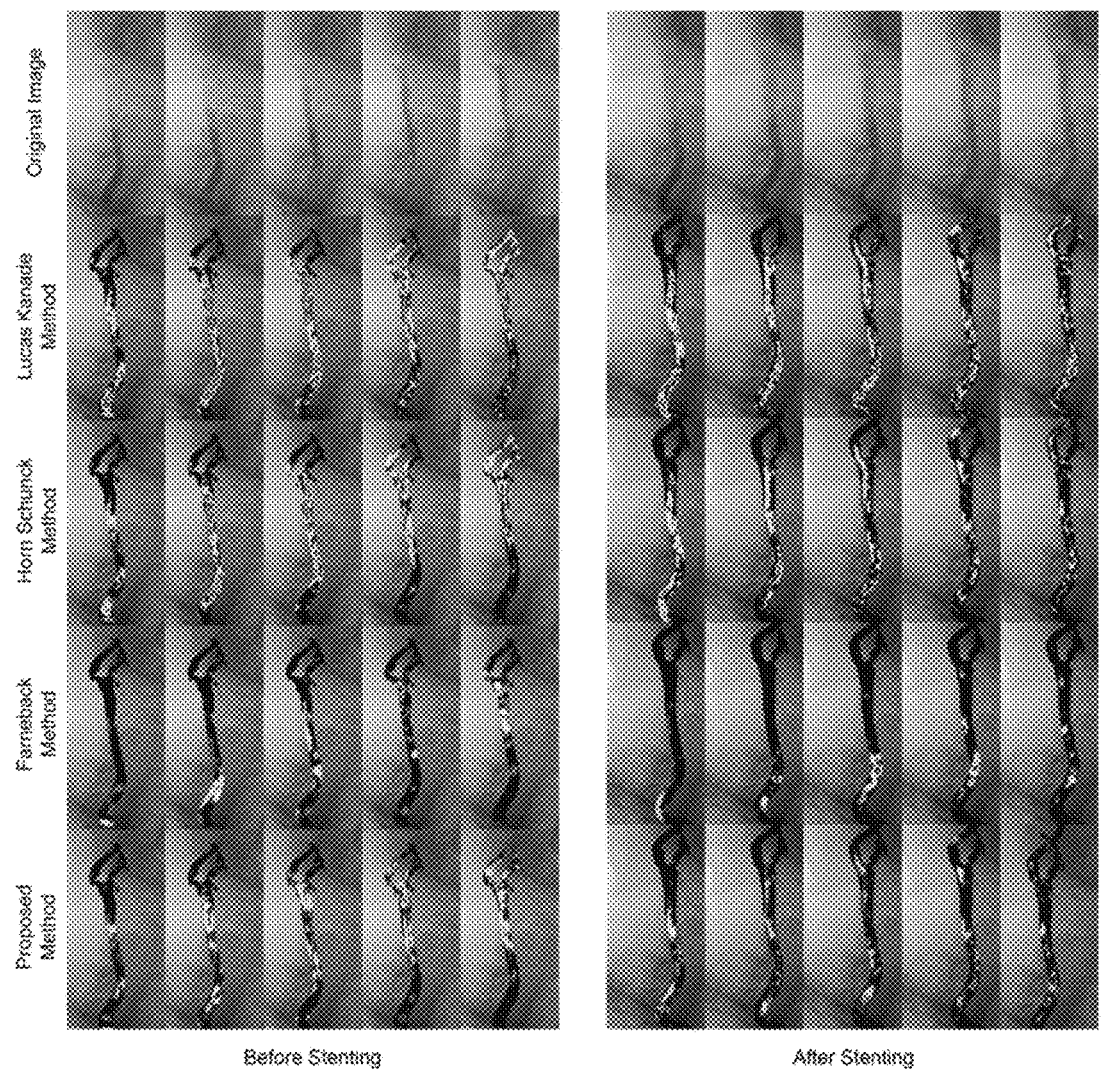
FIG. 4 illustrates five consecutive frames with different optical flow field algorithms at the internal carotid artery; wherein DSA images were obtained before and after stenting.

An example showcase was performed on a special data before and after stenting. The arterial fluid flow profile near stenosis region was obtained by manually selecting a region of interest (ROI). The corresponding mean flow velocity ratio was listed in Table 2 and 3. ROI 1, 2 and 3 were defined as before stenosis, stenosis and after stenosis region (FIG. 3). The temporal mean velocity magnitudes within the ROIs were plotted in FIG. 4. The result was recorded in pixel per second. Five distinctive consecutive frames using four different optical flow methods before and after stenting as displayed in FIG. 5.

TABLE 2

| Patient | Stenosis location | ROI 1 (pixel/s) | ROI 2 (pixel/s) | ROI 3 (pixel/s) | ROI 2/ ROI 1 | ROI 3/ ROI 2 | ROI 3/ ROI 1 |
| --- | --- | --- | --- | --- | --- | --- | --- |
| (a) (Before stenting) | Carotid | 35.2873 | 28.5899 | 21.4475 | 81.0% | 75.0% | 60.8% |
| (a) (After stenting) | Carotid | 25.148 | 19.8213 | 18.1898 | 78.8% | 91.8% | 72.3% |
| (b) | MCA | 24.9039 | 24.2103 | 22.3101 | 97.2% | 92.2% | 89.6% |
| (c) | Carotid | 17.3252 | 12.7342 | 11.2946 | 73.5% | 88.7% | 65.2% |
| (d) | Carotid | 23.8747 | 17.5703 | 14.5736 | 73.6% | 82.9% | 61.0% |
| (e) | Carotid | 12.4096 | 10.7709 | 11.0619 | 86.8% | 102.7% | 89.1% |
| (f) | Carotid | 27.0018 | 17.8127 | 15.403 | 66.0% | 86.5% | 57.0% |
| (g) | MCA | 21.6994 | 19.169 | 22.4869 | 88.3% | 117.3% | 103.6% |

The numerical measurement of flow speed was listed in Table 2 for all 7 patients. For carotid artery stenosis case, stenting could retain more than 11.5% in flow speed.

This disclosure has used a faster imaging temporal interval in 30 FPS. In similar studies, the typical imaging speed is in 6 FPS. Moreover, the combination of local and global optical flow calculation method has a high robustness in velocity field calculation. Blood volume flow rate may also be computed from the velocity profile. The estimation of cardiovascular fluid flow would allow a further hemodynamic analysis, such as computational fluid dynamic simulations.

The ideology of Lucas-Kanade method is to compute a consistent brightness flow within localized neighbors. The method hence is very sensitive to small intensity variations. The rapid algorithm would be applicable to real-time estimations. On contrary, Horn-Schunck method solves the optical flow field in a global point of view. However, the Horn-Schunck method required far more computation cost than the Lucas-Kanade method. The method is also highly affected by the regularization parameter which is associated with the smoothness of optical flow. Due to the long computation time of Horn-Schunck optical flow method, it is not suitable for real-time estimations.

The more advance Farneback method is an approximation of each consecutive frame by quadratic polynomials. This method is efficient and robust by estimating the polynomial expansion under translation transform. The displacement field yields the required optical flow. This accuracy of the velocity flow has been measured using average spatiotemporal angular error. The method has been cross tested with other methods in the original publication. The algorithm could not compete with the most accurate ones, but it takes the advantage of spatiotemporal consistency over consecutive frames. The result is suitable for a two-frame flow estimation, which is exactly the same application of our proposed method. This method, however, assumes a slow varying displacement field which causes in discontinuities in fast moving pixels. But in general, the Farneback's method is a well standard in comparison with the proposed one.

Figure 5:
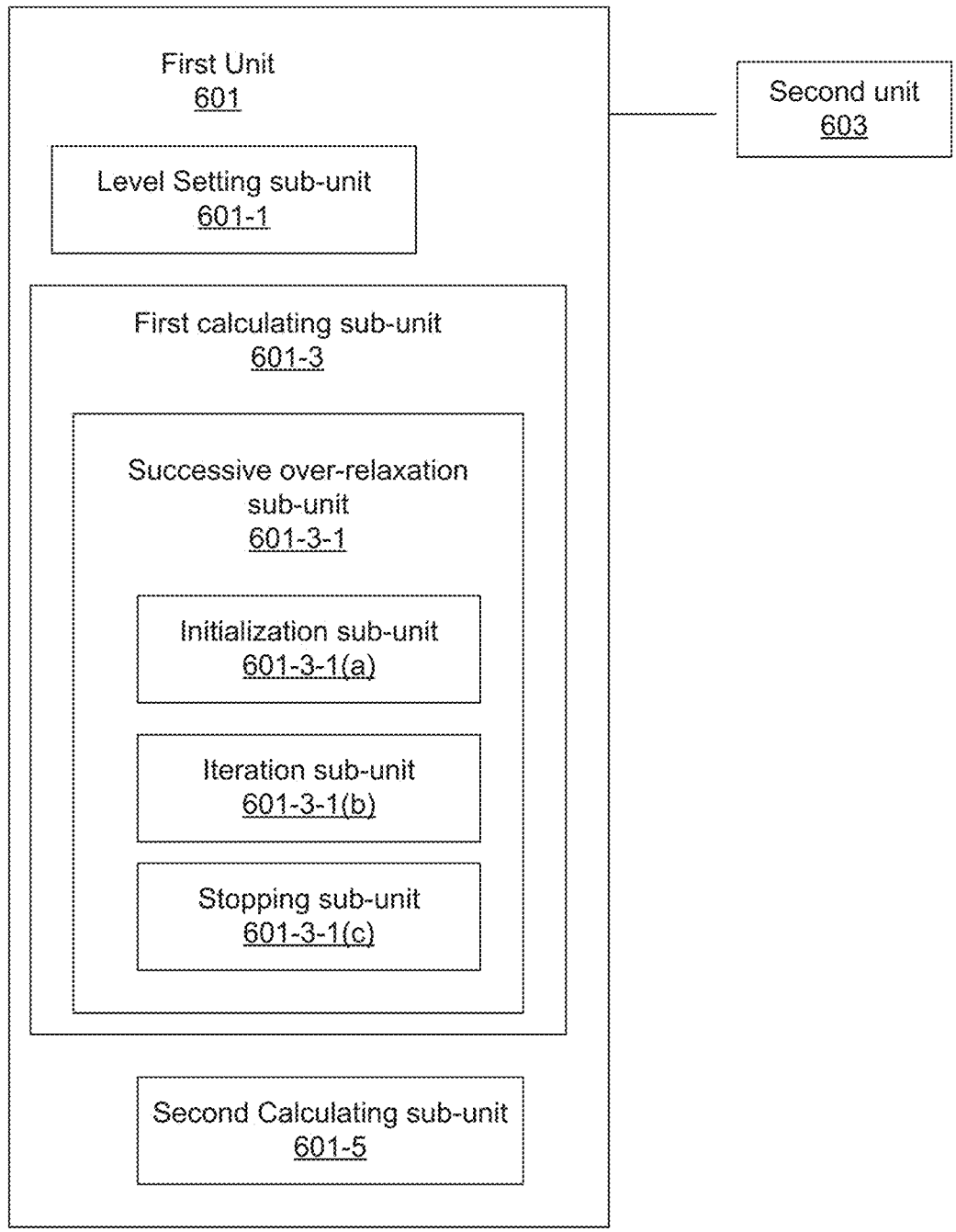
FIG. 5 illustrates a block diagram of an apparatus quantifying vascular fluid motions from DSA according to an embodiment of the disclosure.

In FIGS. 2 and 5, we can observe that the methods behaved differently in localized areas. The Lucas-Kanade method is very sensitive to small area changes. This could cause in high noise level and not robust to general flow cases. Since the Farneback's method adopts the principle of polynomial expansion, the flow field is globally smooth. This may not provide sufficient detail in comparison with other optical flow methods. With the introduction of localized spatial-temporal smoothing term in the CLG optical flow, the proposed method allows a more robust detection globally or locally. In terms of computational speed, as the proposed method was solved by SOR method, it takes 39.4% of the old Horn-Schunck method. The significant improvement in computational speed is comparable with the Farneback's method.

In the stenting case, as the heart rate before and after stenting were different, the interpretation of velocity flow was arguable. The velocity profile was slower after stenting due to heart rate variation. A less biased parameter to be measured was the velocity drop fraction. Since blood flow speed is inversely proportional to the vessel resistance, the degree of artery stenosis could be detected by the respectively flow speed. By assuming blood as an incompressible fluid, the volume flow fraction increased after stenting (Table 2). The result revealed that vascular flow retained 72.3% after stenting. There was a significant drop in peak blood flow velocity from 200 pixels/s to 90 pixels/s after the interventional operation. The hemodynamic properties of this issue should be carefully studied by using CFD simulations.

In the present disclosure, a high spatiotemporal resolution fluid flow quantification is obtained by applying optical flow on DSA images. Comparing with other solutions, there is a significant improvement in temporal resolution from typical 6 FPS to 30 FPS. A new local-global combined algorithm based on nonlinear multiresolution approach, where the localized Lucas-Kanade method was used in similar literature. The new equation solving technique (SOR method) showed the superiority over past method in terms of computation speed, in which reduced from 60 min to 10 min for 1 analysis with a typical desktop PC. The experimental data shows sufficient robust and fast velocity provided a new quantification approach for cardiovascular fluid flow.

Figure 6:
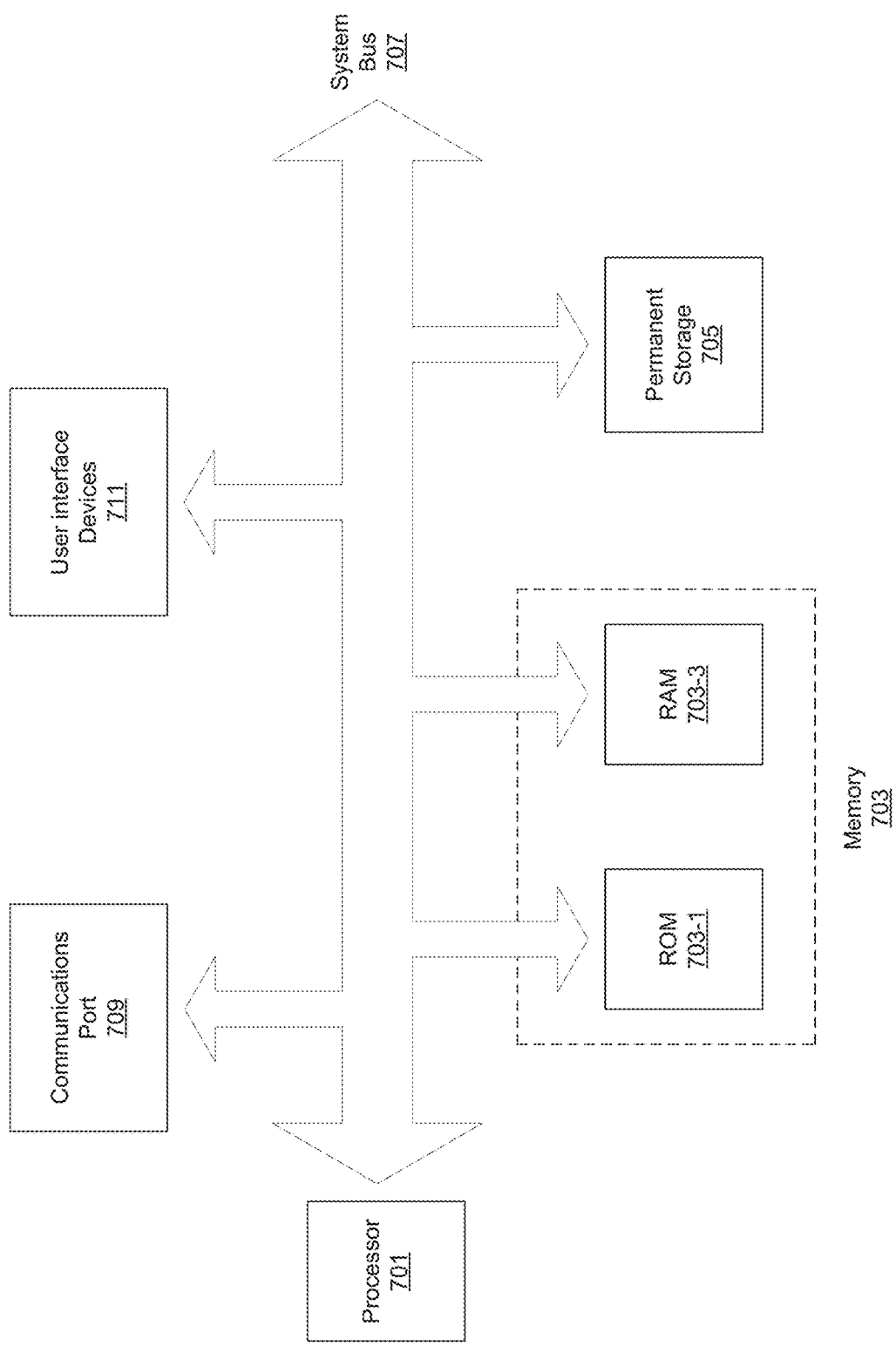
FIG. 6 illustrates a schematic diagram of an apparatus quantifying vascular fluid motions from DSA according to an embodiment of the disclosure.

In FIG. 6, an apparatus 600 for quantifying vascular fluid motions from DSA is illustrated. The apparatus 600 comprises a first unit 601 configured to calculate an optical flow field between two temporal consecutive DSA images; and a second unit 603 configured to estimate a displacement of blood or tissue between the two temporal consecutive DSA images from the calculated optical flow field, wherein the optical flow field is calculated by solving a minimization problem of a CLG energy function, wherein the CLG energy function combines the temporally extended variant of Horn-Schunck approach with Lucas-Kanade approach non-linearly in spatiotemporal approach. The first unit comprises a level setting sub-unit 601-1 configured to set a plurality of image pyramid levels from coarse to fine; a first calculating sub-unit 601-3 configured to calculate an optical flow increment between the two temporal consecutive DSA images which minimizes the CLG energy function at each of the plurality of image pyramid levels; and a second calculating sub-unit 601-5 configured to calculate an interpolated sum of the optical flow increment fields calculated over all the plurality of image pyramid levels so as to obtain the optical flow field. The CLG energy function is established by extending the classically Horn-Schunck approach. A Gaussian smoothing term is introduced to the energy function where the original energy term is an estimation to the optical flow increment and is determined by the gradient of image intensity field. The intensity field is extended from spatial field to the spatial-temporal field according to the two temporal consecutive DSA images. In Lucas-Kanade approach the localized flow is assumed to be constant and represented as a Gaussian kernel convolution in the CLG energy function. The first calculating sub-unit 601-3 comprises a successive over-relaxation sub-unit 601-3-1 configured to solve the minimization problem of the CLG energy function by successive over-relaxation approach. The successive over-relaxation sub-unit 601-3-1 comprises a initialization sub-unit 601-3-1(a) configured to setting an initial optical flow field, a iteration sub-unit 601-3-1(b) configured to iteratively renew the optical flow field, and a stopping sub-unit 601-3-1(c) configured to stop the iteration and obtain a final optical flow field at current pyramid level when the criterion for stopping iteration is met.

According to other embodiments of the present disclosure, apparatuses for quantifying vascular fluid motions from DSA are provided. The apparatuses correspond to the methods proposed in the present disclosure, and are used for executing these methods. As illustrated in FIG. 7, the apparatuses described herein may comprise a processor 701, a memory 703 for storing program data and executing the program data, a permanent storage unit 705, such as a disk drive, a system bus 707, a communications port 709 for handling communications with external devices, and user interface devices 711, including a touch panel, keys, buttons, etc. When software modules or algorithms are involved, these software modules may be stored as program instructions or computer readable codes executable on a processor on a computer-readable medium. Examples of the computer readable recording medium include magnetic storage media (e.g., read-only memory (ROM) 703-1 in FIG. 7, random-access memory (RAM) 703-3 in FIG. 7, floppy disks, hard disks, etc.), and optical recording media (e.g., CD-ROMs, or Digital Versatile Discs (DVDs)). The computer readable recording medium can also be distributed over network coupled computer systems so that the computer readable code is stored and executed in a distributive manner. This media can be read by the computer, stored in the memory, and executed by the processor.

Exemplary embodiments of the present disclosure may be described in terms of functional block components and various processing steps. Such functional blocks may be realized by any number of hardware and/or software components configured to perform the specified functions. For example, exemplary embodiments may employ various integrated circuit (IC) components, e.g., memory elements, processing elements, logic elements, look-up tables, and the like, which may carry out a variety of functions under the control of one or more microprocessors or other control devices. Similarly, where the elements are implemented using software programming or software elements, the embodiments described herein may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the exemplary embodiments described herein could employ any number of conventional techniques for electronics configuration, signal processing and/or control, data processing and the like. The words "mechanism," "element," "means," and "configuration" are used broadly and are not limited to mechanical or physical embodiments, but can include software routines in conjunction with processors, etc.

The particular implementations shown and described herein are illustrative examples and are not intended to otherwise limit the scope of the present disclosure in any way. For brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical apparatus.

The use of the terms "a" and "an" and "the" and similar referents in the context of describing the present disclosure (especially in the context of the following claims) are to be construed to cover both the singular and the plural expressions. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The present disclosure is not limited to the described order of the steps. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to one of ordinary skill in the art without departing from the spirit and scope.

The exemplary embodiments should be considered in descriptive sense only and not for purposes of limitation. Descriptions of features or aspects within each embodiment should typically be considered as available for other similar features or aspects in other embodiments.

While the present disclosure has been particularly shown and described with reference to exemplary embodiments thereof, it will be understood by those of ordinary skill in the art that various changes in form and details may be made therein without departing from the spirit and scope of the present disclosure.

What is claimed is:

1. A method for quantifying vascular fluid motions from digital subtraction angiography (DSA) images, comprising:
   calculating an optical flow field between two temporal consecutive DSA images; and
   estimating a displacement of blood or tissue between the two temporal consecutive DSA images from the calculated optical flow field,
   wherein the optical flow field is calculated by solving a minimization problem of a combined local global (CLG) energy function, wherein the CLG energy function combines the temporally extended variant of Horn-Schunck approach with Lucas-Kanade approach non-linearly in spatiotemporal approach,
   wherein the CLG energy function is established by:
      establishing an energy function by Horn-Schunck approach, which includes an energy term and a regularization term, wherein the energy term is determined by an estimated optical flow increment field and a gradient of an intensity field, and the intensity field is extended from a spatial field to a spatial-temporal field according to the two temporal consecutive DSA images; and
      transforming the gradient of the intensity field in a spatial-temporal vector space to a localized spatial-temporal derivative smoothing tensor by a convolution kernel, wherein the localized spatial-temporal derivative smoothing tensor is defined as $J_\rho(\nabla_3 I) = K_\rho * (\nabla_3 I \nabla_3 I^T)$, wherein $\rho$ denotes for a localized constant flow assumed in Lucas-Kanade approach, $K_\rho$ denotes for a Gaussian kernel with standard deviation $\rho$, I denotes for the intensity field of DSA images, $\nabla_3 I = [I_x, I_y, I_t]^T$, denoting for the gradient of the intensity field of DSA images, wherein $$I_x = \frac{\partial I}{\partial x}, I_y = \frac{\partial I}{\partial y} \text{ and } I_t = \frac{\partial I}{\partial t},$$

x and y denote for a two-dimensional spatial position, t denotes for a time.

2. The method according to claim 1, wherein calculating the optical flow field comprising:
   setting a plurality of image pyramid levels from coarse to fine;
   at each of the plurality of image pyramid levels, calculating an optical flow increment between the two temporal consecutive DSA images which minimizes the CLG energy function; and
   calculating an interpolated sum of the optical flow increment fields calculated over all the plurality of image pyramid levels so as to obtain the optical flow field.

3. The method according to claim 2, wherein the CLG energy function is further established by:
wrapping the intensity field by the estimated optical flow increment field.

4. The method according to claim 3, further comprising:
assuming a localized flow to be constant and representing the localized flow as a Gaussian kernel convolution in the CLG energy function.

5. The method according to claim 3, wherein the regularization term is determined by a regularization parameter and an optical flow field wrapped by the estimated optical flow increment field according to the two temporal consecutive DSA images.

6. The method according to claim 5, wherein at each level of image pyramid, the localized spatial-temporal derivative smoothing tensor is further defined as a term determined by $\nabla_3 I(p+\delta w^{(m)})$,
wherein p denotes for a spatial-temporal position including the two-dimensional spatial position and the time point, $\delta w^{(m)}$ denotes for a estimated optical flow increment field at an image pyramid level m, $I(p+\delta w^{(m)})$ denotes for the second DSA image wrapped by $\delta w^{(m)}$.

7. The method according to claim 6, wherein at each level of image pyramid, the regularization term is defined as $\alpha(\|\nabla(w^{(m)}+\delta w^{(m)})\|)^2$,
wherein $\alpha$ denotes for the regularization parameter, $w^{(m)}$ denotes for a optical flow field at the image pyramid level m, $w^{(m)}+\delta w^{(m)}$ denotes for the optical flow field at the image pyramid level m wrapped by $\delta w^{(m)}$.

8. The method according to claim 7, wherein the minimization problem of the CLG energy function is solved by successive over-relaxation approach.

9. The method according to claim 8, wherein the successive over-relaxation approach comprising: at each image pyramid level,
setting an initial optical flow field;
iteratively renewing the optical flow field, wherein in each iterative step, a new velocity at pixel i within the image domain is determined by a current velocity at the pixel i, relaxation parameter $\omega$, a current velocity at neighbor pixels of the pixel i, the localized spatial-temporal derivative smoothing tensor, and the regularization term $\alpha$; and
stopping the iteration and obtaining a final optical flow field at current pyramid level when the criterion for stopping iteration is met.

10. An apparatus for quantifying vascular fluid motions from digital subtraction angiography (DSA) images, comprising:
at least one processor; and
a memory storing instructions, the instructions when executed by the at least one processor, cause the at least one processor to perform operations, the operations comprising:
calculating an optical flow field between two temporal consecutive DSA images; and
estimating a displacement of blood or tissue between the two temporal consecutive DSA images from the calculated optical flow field,
wherein the optical flow field is calculated by solving a minimization problem of a combined local global (CLG) energy function, wherein the CLG energy function combines the temporally extended variant of Horn-Schunck approach with Lucas-Kanade approach non-linearly in spatiotemporal approach, wherein the CLG energy function is established by:
establishing an energy function by Horn-Schunck approach, which includes an energy term and a regularization term, wherein the energy term is determined by an estimated optical flow increment field and a gradient of an intensity field, and the intensity field is extended from a spatial field to a spatial-temporal field according to the two temporal consecutive DSA images; and
transforming the gradient of the intensity field in a spatial-temporal vector space to a localized spatial-temporal derivative smoothing tensor by a convolution kernel, wherein the localized spatial-temporal derivative smoothing tensor is defined as $J_\rho(\nabla_3 I)=K_\rho*(\nabla_3 I \nabla_3 I^T)$, wherein $\rho$ denotes for a localized constant flow assumed in Lucas-Kanade approach, $K_\rho$ denotes for a Gaussian kernel with standard deviation $\rho$, I denotes for the intensity field of DSA images, $\nabla_3 I=[I_x, I_y, I_t]^T$, denoting for the gradient of the intensity field of DSA images, wherein $$I_x = \frac{\partial I}{\partial x}, I_y = \frac{\partial I}{\partial y} \text{ and } I_t = \frac{\partial I}{\partial t},$$

x and y denote for a two-dimensional spatial position, t denotes for a time.

11. The apparatus according to claim 10, wherein the operation of calculating the optical flow field comprises:
setting a plurality of image pyramid levels from coarse to fine;
calculating an optical flow increment between the two temporal consecutive DSA images which minimizes the CLG energy function at each of the plurality of image pyramid levels; and
calculating an interpolated sum of the optical flow increment fields calculated over all the plurality of image pyramid levels so as to obtain the optical flow field.

12. The apparatus according to claim 11, wherein the CLG energy function is further established by wrapping the intensity field by the estimated optical flow increment field.

13. The apparatus according to claim 12, wherein the operations further comprise assuming a localized flow to be constant and representing a localized flow as a Gaussian kernel convolution in the CLG energy function.

14. The apparatus according to claim 12, wherein the regularization term is determined by a regularization parameter and an optical flow field wrapped by the estimated optical flow increment field according to the two temporal consecutive DSA images.

15. The apparatus according to claim 14, wherein at each level of image pyramid, the localized spatial-temporal derivative smoothing tensor is further defined as a term determined by $\nabla_3 I(p+\delta w^{(m)})$,
wherein p denotes for a spatial-temporal position including the two-dimensional spatial position and the time point, $\delta w^{(m)}$ denotes for a estimated optical flow increment field at an image pyramid level m, $I(p+\delta w^{(m)})$ denotes for the second DSA image wrapped by $\delta w^{(m)}$.

16. The apparatus according to claim 15, wherein at each level of image pyramid, the regularization term is defined as $\alpha(\|\nabla(w^{(m)}+\delta w^{(m)})\|)^2$,
wherein $\alpha$ denotes for the regularization parameter, $w^{(m)}$ denotes for a optical flow field at the image pyramid level m, $w^{(m)}+\delta w^{(m)}$ denotes for the optical flow field at the image pyramid level m wrapped by $\delta w^{(m)}$.

17. The apparatus according to claim 16, wherein:
the minimization problem of the CLG energy function is solved by successive over-relaxation approach.

18. The apparatus according to claim 17, wherein the successive over-relaxation approach comprises: at each image pyramid level,
   setting an initial optical flow field;
   iteratively renewing the optical flow field, wherein in each iterative step, a new velocity at pixel i within the image domain is determined by a current velocity at the pixel i, relaxation parameter ω, a current velocity at neighbor pixels of the pixel i, the localized spatial-temporal derivative smoothing tensor, and the regularization term α; and
   stopping the iteration and obtaining a final optical flow field at current pyramid level when the criterion for stopping iteration is met.

* * * * *